United States Patent [19]

Reynolds

[11] 4,407,283

[45] Oct. 4, 1983

[54] SELF-INJECTING SYRINGE

[75] Inventor: Francis D. Reynolds, Redmond, Wash.

[73] Assignee: Dale C. Grier, Bellevue, Wash.

[21] Appl. No.: 312,535

[22] Filed: Oct. 19, 1981

[51] Int. Cl.³ ............................................. A61M 5/00
[52] U.S. Cl. ..................................... 604/136; 604/233
[58] Field of Search ............... 128/218 R, 218 F, 220, 128/221, 234, 213, 215, 216

[56] References Cited

U.S. PATENT DOCUMENTS

| 98,478 | 1/1870 | Eccleston | 128/218 F |
|---|---|---|---|
| 922,331 | 5/1909 | Quarles | 128/218 F |
| 1,845,036 | 2/1932 | Busher | 128/218 F |
| 1,921,034 | 8/1933 | La Marche | 128/218 F |
| 2,565,081 | 8/1951 | Maynes | 128/218 F |
| 2,664,086 | 12/1953 | Transue | 128/218 F |
| 3,224,445 | 12/1965 | Melott | 128/218 F |
| 3,583,399 | 6/1971 | Ritsky | 128/218 D |
| 3,605,743 | 9/1971 | Arce | 128/218 F |
| 3,605,744 | 9/1971 | Dwyer | 128/218 F |
| 3,656,472 | 4/1972 | Moura | 128/218 F |
| 3,702,608 | 11/1972 | Tibbs | 128/218 F |
| 3,880,163 | 4/1975 | Ritterskamp | 128/218 F |
| 4,202,314 | 5/1980 | Smirnov et al. | 128/218 F |

Primary Examiner—John D. Yasko

[57] ABSTRACT

A squeezing finger pressure is exerted on a trigger mechanism carried by a finger-grip portion of a hypodermic syringe. The depressed trigger mechanism displaces a V-shaped lock spring inwardly, moving a bight portion of the spring out from locking engagement with a lock opening. This frees a compressed compression spring allowing it to drive an internal bushing, a cartridge within a barrel portion of the syringe, a second bushing at the front end of the syringe, and a needle forwardly together, relative to the finger-grip body and the barrel of the syringe. This is done for the purpose of penetrating a needle into tissue in which an injection is to be made.

8 Claims, 8 Drawing Figures

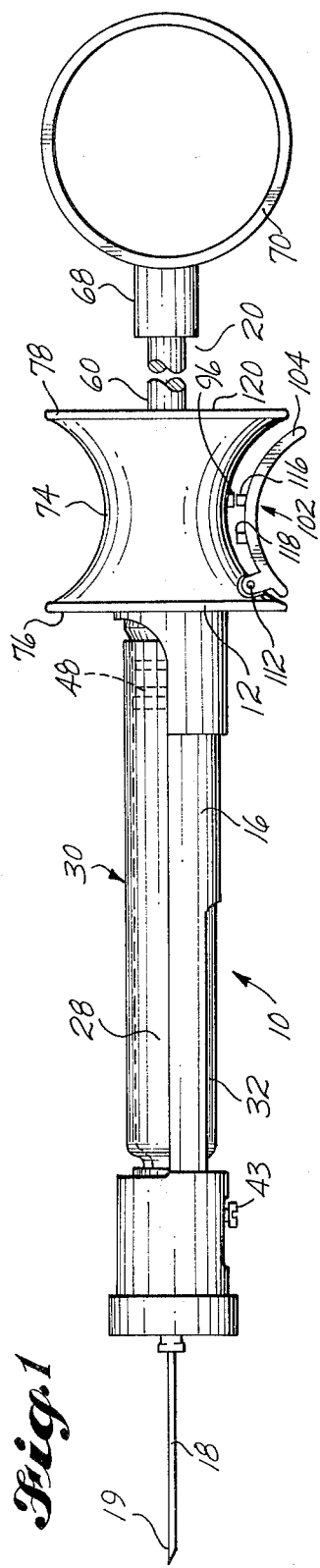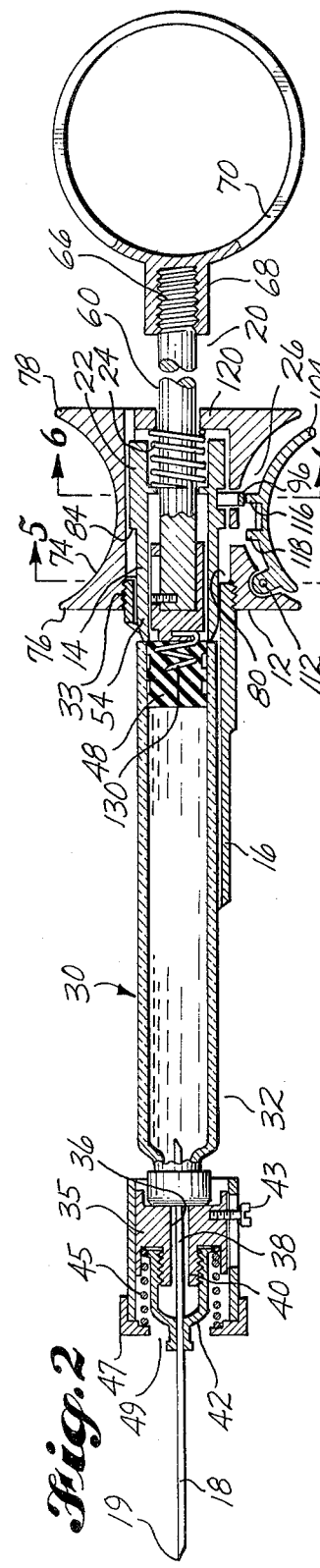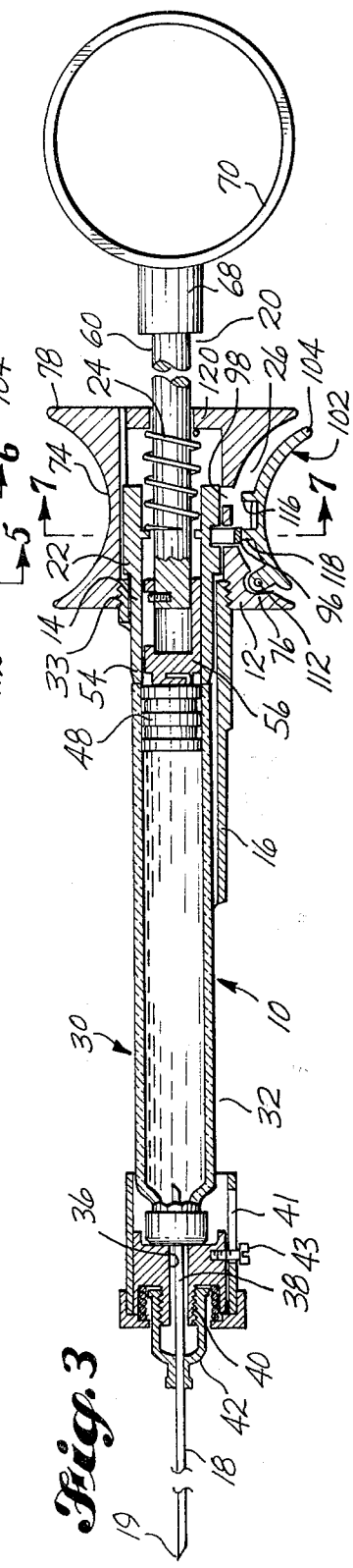

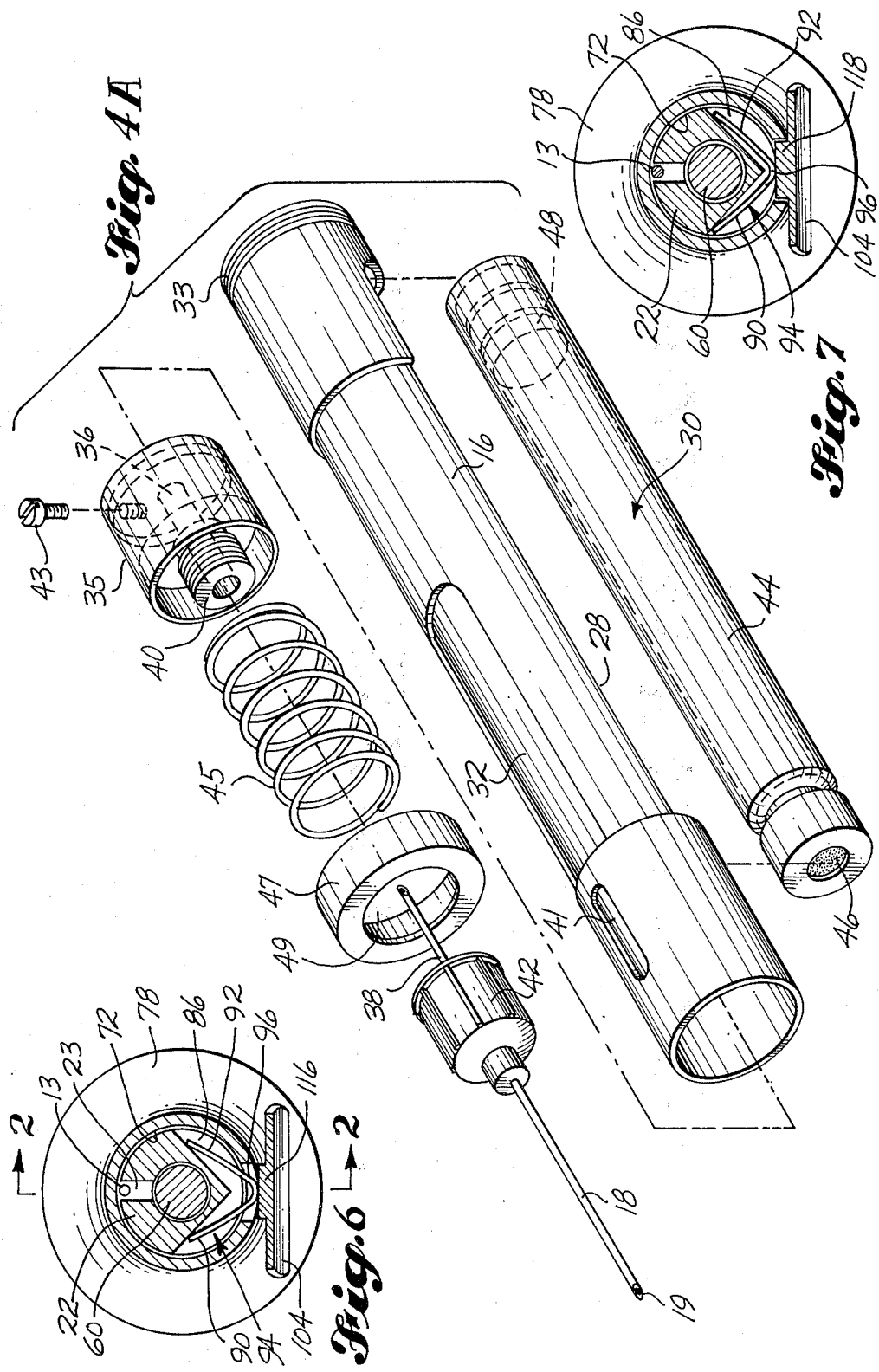

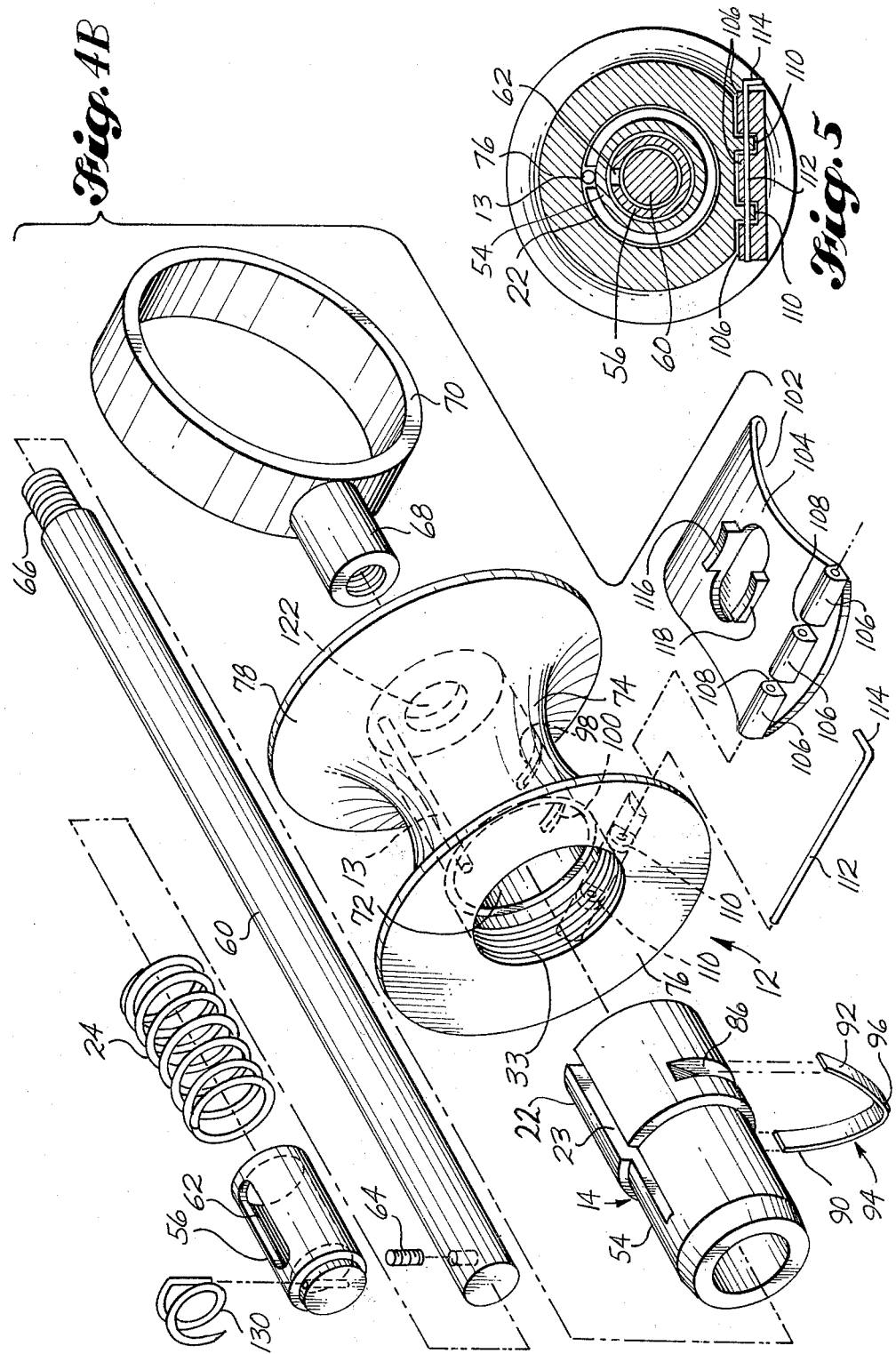

4,407,283

SELF-INJECTING SYRINGE

TECHNICAL FIELD

This invention relates to hypodermic syringes, and in particular to improvements in self-injecting syringes.

BACKGROUND ART

The following patents disclose various types of self-injecting syringes: U.S. Pat. No. 98,478, granted Jan. 4, 1870, to Charles H. Eccleston; U.S. Pat. No. 922,331, granted May 18, 1909, to Thomas M. Quarles; U.S. Pat. No. 1,845,036, granted Feb. 16, 1932, to Herbert H. Busher; U.S. Pat. No. 1,921,034, granted Aug. 8, 1933, to Norman O. La Marche; U.S. Pat. No. 2,664,086, granted Dec. 29, 1953, to Gerald O. Transue and U.S. Pat. No. 3,605,743, granted Sept. 20, 1971, to Raul O. Arce.

U.S. Pat. No. 3,224,445, granted Dec. 21, 1965, to Norman W. Melott and U.S. Pat. No. 3,583,399, granted June 8, 1971, to Anthony F. Ritsky, both disclose syringes which are adapted for performing the procedure known as "aspiration". The procedure known as "aspiration" is defined in these patents.

The various patents introduced above speak for themselves and therefore do not need to be specifically described in any detail. However, such patents, and the various patents cited against them, should be carefully considered for the purpose of putting the present invention into proper perspective relative to the prior art.

DESCRIPTION OF THE INVENTION

One aspect of the present invention is to provide a self-injecting syringe. In basic construction, such syringe comprises a finger-grip body having first and second ends and an annular sidewall defining an inner chamber. It also includes an outer surface grip portion adapted to be gripped by fingers of a user. A first end portion of a first bushing is slidably received within said chamber. A second end portion of the first bushing is extendable axially from the first end portion out through the first end of the body. Stop means prevents movement of said bushing out from the body. An end wall is provided at the second end of the body. A first end of a syringe barrel is connected to the first end of the finger-grip body. The syringe barrel includes an axially movable second bushing at its opposite end which is adapted to carry a standard hypodermic needle. A first compression spring is provided between a nose cap and the second bushing. A second compression spring is provided within the inner chamber. One of its ends bears against the first bushing and its opposite end bears against the end wall. The second compression spring normally biases the first bushing into a forward stop position. A releasable lock means is provided within the body. It includes a lock member operable to lock the busing into a retracted position, with the compression spring compressed and the bushing spaced axially from the stop means. A release trigger is contractable by a finger positioned on the grip portion of the body. Finger pressure on the release trigger will unlock the lock means, releasing the compression spring and allowing it to drive the first bushing, the syringe cartridge, the second bushing and the needle axially relative to the body and the barrel until the first bushing is in its stop position. This movement is attended by penetration of the needle into the tissue into which an injection is to be made.

In accordance with the preferred form of the invention, the releasable lock means comprises a V-shaped latch spring retained within a side cavity in the first bushing, having a V-shaped floor. The angle between leg portions of the leaf spring is an acute angle and the angle between the two portions of the cavity floor is a larger angle. As a result, when the spring is relaxed and the ends of the leg portions are against the floor surfaces of the cavity, the apex or bight portion of the spring wants to be located radially outwardly from the side boundary of the first bushing. The finger-grip body includes a sidewell opening into which the bight of the spring projects when the first bushing is retracted and the compression spring which it contacts is compressed.

In preferred form, the releasable lock means includes a trigger member carried by the finger-grip body. When depressed, such member exerts an inward force on the bight of the latch spring, moving such bight out from engagement with the sidewall opening. As soon as the leaf spring clears the sidewall opening, the stored energy in the compression spring drives the first bushing endwise from its retracted to its extended position. The first bushing rests against the rear end of a cartridge within the syringe barrel. Thus, the cartridge is moved forwardly by the first bushing as it moves.

Also in preferred form, the trigger member is in the form of a plate which is hinge connected to the finger-grip body at its forward end. Such plate includes a radially inwardly directed lug which is in radial alignment with the lock opening in the sidewall of the finger-grip body. The trigger-plate is preferably longitudinally curved. This curvature and the location of the hinge facilitates swinging movement of the trigger-plate upon the application of a squeezing finger pressure on the plate and the body.

In preferred form, the trigger-plate carries a second radially inwardly projecting lug which is in radial alignment with a second lock opening in the sidewall of the finger-grip body. The bight of the leaf spring is positioned to enter the second opening when the first bushing is in its extended position. The second lug provides a way of depressing the leaf spring for moving it out of locking engagement with the second opening when it is desired to again retract the first bushing. When the latch spring is engaged in the second opening, it serves as a means for coupling the first bushing and the finger-grip body together.

These and other objects, features, characteristics and advantages pertaining to and inherent in the present invention will be apparent from the following description of a typical and therefore non-limitive embodiment of the invention.

BRIEF DESCRIPTION OF THE DRAWING

Referring to the several drawing figures, wherein like numerals refer to like parts throughout, and wherein:

FIG. 1 is a side elevational view of a hypodermic syringe embodying features of the present invention, such view showing the shaft of the plunger broken away;

FIG. 2 is a longitudinal sectional view of the syringe shown by FIG. 1, taken substantially along line 2—2 of FIG. 6, and showing the extendable elements of the syringe in a retracted position relative to the finger-grip body and the barrel, and showing the injection spring compressed and the releasable lock means locked;

FIG. 3 is a view like FIG. 2, but showing the releasable lock means released, and the cartridge and needle moved forwardly relative to the finger-grip body;

FIG. 4A is an exploded isometric view of the forward portion of the syringe that is shown by FIGS. 1-3;

FIG. 4B is an exploded isometric view of the rear portion of the syringe shown by FIGS. 1-3;

FIG. 5 is a cross-sectional view taken substantially along line 5—5 of FIG. 2, showing the hinge connection of the trigger mechanism to the finger-grip body;

FIG. 6 is a cross-sectional view taken substantially along line 6—6 of FIG. 2, showing the lock spring in a lock position;

FIG. 7 is a cross-sectional view taken substantially along line 7—7 of FIG. 3, but showing the trigger mechanism depressed and the lock spring moved inwardly into a release position.

BEST MODE FOR CARRYING OUT THE INVENTION

Referring again to the several figures of the drawing, the illustrated embodiment 10 comprises a finger-grip body 12, a rear bushing 14, a syringe barrel 16, an injection needle 18 and a plunger 20.

The finger-grip body serves as a housing for the rear portion 22 of bushing 14, a compression spring 24 and a releasable lock mechanism 26.

Barrel 16 is essentially like the barrel 17 of the syringe shown by U.S. Pat. No. 3,583,399 and the barrel 10 of the syringe disclosed by U.S. Pat. No. 3,224,445. It includes a side loading window 28 for a cartridge 30 and an opposite side observation window 32. Barrel 16 is connected at its rear end to the body 12, such as by a screw thread connection 33.

Cartridge 30 is of conventional construction and comprises a cylindrical sidewall 44, a diaphragm wall closure 46 at its forward end, and a piston type closure 48 at its rearward end.

The rear end portion of barrel 16 preferably includes exterior threads 33 which mate with interior threads provided at the forward end of body 12.

A slidable plunger head 56 is housed within the front end portion of the bushing 14. It includes an axial socket sized to snugly receive a forward portion of the plunger shaft 60. A pin slot 62 is formed in a sidewall portion of the socket. A pin 64 rides within the slot 62. Pin 64 is shown in the from of a screw 64 which threads into a side opening provided in the front end portion of plunger shaft 60.

The rear end portion 66 of plunger shaft 60 is externally threaded and makes threaded engagement with internal threads formed in a forward tubular extension 68 of a thumb ring 70.

In preferred form, the finger-grip body 12 is formed to include an inner chamber 72, which may be cylindrical in shape and which extends longitudinally of the body 12. Body 12 comprises an annular sidewall 74, a forward end 76 and a rearward end 78. The rear end of barrel 16 provides a radial stop surface 80 (FIG. 2).

The rear portion 22 of bushing 14 is larger in cross-sectional dimension (e.g. diameter) than the forward portion 54 of bushing 14. As a result, a stop shoulder 84 (FIG. 2) is formed where the two end portions of the bushing 14 meet.

As best shown by FIGS. 6 and 7, an intermediate portion of bushing 14 includes a two-sided cavity 86 cut into a portion of the periphery of bushing 14. The two side portions of the cavity 86 receive the end portions 90, 92 of a V-shaped leaf spring 94. A bight portion 96 of spring 94 is directed radially outwardly. As shown by FIG. 6, when the spring 94 is relaxed, its bight portion 96 projects outwardly into one or the other of a pair of side openings 98, 100 formed in the sidewall 74 of body 12. The openings 98, 100 are spaced apart axially. As shown by FIG. 2, when the bushing 14 is retracted, and the compression spring 24 is compressed, the bight 96 is aligned with the rear opening 98. As shown by FIG. 3, when the bushing 14 is in its forward position, the bight 96 is aligned with the forward opening 100.

According to an aspect of the invention, the body 12 is provided with a trigger mechanism 102. As best shown by FIG. 4B, trigger mechanism 102 has a curved plate like body 104 which is longitudinally curved to closely match the longitudinal curvature of the finger-grip portion 74 of body 12. A mounting hinge is provided at the forward end of member 104. In preferred form, the hinge is in the nature of a knuckle hinge and comprises a plurality of lugs 106 formed on member 104 and spaced apart to receive within spaces 108 a pair of lugs 110 formed on body portion 76. A hinge pin 112 extends axially through aligned openings in the lugs 106, 110. Hinge pin 112 includes a bent end portion 114 for preventing its movement in one direction through the openings. The opposite end is left straight so that the pin 112 can readily be removed when it is desired to disassemble the trigger mechanism.

The inner side of plate 104 includes a pair of inwardly projecting lugs 116, 118 which are axially spaced apart the same distance as the openings 98, 100. As best shown by FIGS. 2, 3, 6 and 7, the lugs 116, 118 are in radial alignment with the openings 98, 100 so that they can be moved down into the openings 98, 100 by an inward swinging movement of the trigger mechanism 102.

Bushing 14 is prevented from rotating in position within body 12. For example, a longitudinal groove 23 may be formed in an outer sidewall portion of bearing 14 for receiving a key 13 carried by body 12.

As best shown by FIGS. 2 and 3, the rear end portion of inner chamber 72 is closed by an end wall 120. End wall 120 includes a central opening 122 (FIG. 4B) sized to snugly receive the plunger shaft 60. Opening 122 is axially aligned with a central passageway in the bushing 14. The compression spring 24 is housed within chamber 72. Its forward end rests against a rear surface of a flange formed within bushing 14 and its rear end rests against the front surface of end wall 120. Compression spring 24 also surrounds the shaft portion 60 of plunger 20.

Preferably, the forward end 56 of plunger 20 carries a helical corkscrew like hook 130. Plunger 20 is made to be rotatable and the head 56 is made to be rotatable with it.

As stated above, the rear end of barrel 16 is connected to the finger-grip body 12 by a screw thread connection 33. The front end of the barrel 16 includes an end cap 47 that engages the front end of a forward sidewall portion of the barrel 16. A bushing 35 is housed within the space defined by the end cap 47 and the forward sidewall portion. The bushing 35 has an externally threaded head portion 40 which threadedly engages an internally threaded base portion 42 of a hypodermic needle. The end cap 47 has a central axial opening 49 for receiving said threaded base portion 42 and allowing said portion 42 to move axially with respect to end cap 47 (see FIGS. 2 and 3). The bushing 35 also has a central axial passageway 36 for receiving an inner hollow shaft portion 38 of the needle. When a hypodermic needle is installed, the inner fluid receiving portion 38 of the needle 18 projects axially rearwardly through passageway 36 into the cartridge chamber of the barrel 16.

The forward sidewall portion of the barrel 16 includes a longitudinal slot 41. The shaft of a screw 43 rides within the slot 41. The outer end of the shaft of the screw 43 engages the bushing 35 to secure the bushing 35 within the barrel 16. However, the screw 43 can move axially within the slot 41 to permit axial movement of the bushing 35 in response to movement of the bushing 14 from its retracted to its extended position.

A coil spring 45 is disposed about the head portion 40 of the bushing 35 and the base portion 42 of the hypodermic needle. One end of the spring 45 abuts the inner surface of the end cap 47, and the other end of the spring 45 abuts a radial surface portion of the bushing 35. The structure of the front end of the barrel 16 is most clearly shown in FIGS. 2 and 3 and will be further illuminated by the following description of the loading and operation of the syringe 10.

The cartridge 30, including a fluid to be injected, is loaded in the following manner: with trigger depressed, the plunger 20 is pulled rearwardly to move the bushing 14 rearwardly, to in that manner compress spring 24. Then, the cartridge 30 is moved through the window 28 and set into place. As it is being installed, the cartridge 30 moves bushing 35 forwardly until the cartridge is within its chamber. Then the spring 45 biases both the bushing 35 and the cartridge 30 rearwardly. Next, the plunger 20 is rotated to cause the helical hook 130 to screw its way into the plunger cork 48.

Next the needle 18 is installed. During installation the slant cut rear end of needle portion 38 pierces the diaphragm wall 46, to in that manner communicate the liquid inside of cartridge 30 with the passageway which extends through the injection needle 18. The spring 45 maintains the pressure on the cartridge 30, holding it in place.

The self-injecting mechanism of the present invention will now be described:

Starting with the various components of the self-injecting mechanism positioned as shown in FIG. 3, but without a cartridge 30 in the chamber of the barrel, the driving mechanism housed within the body 12 can be retracted into its "cocked" position by the user simply by moving the plunger rearwardly so that the pin 64 will contact the rear end of slot 62. Further rearward movement of plunger 20 will cause the plunger head 56 to contact the internal flange within the bushing 14, moving bushing 14 rearwardly against the force of compression spring 24. Of course, at the start of this movement, the trigger plate 104 is depressed for the purpose of moving lug 118 against the bight 96 of lock spring 94, for the purpose of depressing the spring inwardly an amount sufficient to cause bight 96 to clear the side edges of opening 100, and allow the rearward movement of bushing 14. Once bushing 14 has been retracted, finger pressure is removed from the trigger plate 104, so that the bight 96 of lock spring 94 will be moved outwardly into the spring lock opening 98. The parts are now in their "cocked" position. With a cartridge within the barrel chamber, the syringe is now ready to use.

Prior to injection, the middle and index fingers of the user are positioned on opposite sides of the body wall 74. The one finger is loosely positioned on the trigger plate 104 and the other finger is positioned diametrically opposite it across the body 12. The thumb is loosely placed within the thumb ring 70. Next, the needle point 19 is set against the particular tissue into which an injection is to be made. The user then applies a squeezing pressure by moving the two fingers together. This squeezing movement causes the fingers to depress the trigger plate 104 an amount sufficient to displace bight 96 of the lock spring 94 from the opening 98. When this happens, stored energy within compression spring 24 is freed to act against the bushing 14. Extension of spring 24 is immediate and quick and it results in a fast forward movement of the bushing 14, the cartridge 30, the needle 18 and the bushing 35, all relative to the body 12 and the barrel 16, and a piercing of the needle point 19 into the tissue. Bushing 14 and the parts carried thereby are moved forwardly until the bushing 14 is in a stop position. Any additional penetration of the needle that might be necessary is accomplished by the user merely pushing the entire syringe towards the tissue until sufficient additional penetration is achieved.

The forward location of hinge pin 112 facilitates inward movement of the trigger plate 104 by the squeezing action on the curved rear portion of plate 104.

The aspirating feature will now be described:

The presence of the spiral, corkscrew type hook 130, provides a way of forming a firm and sure connection between the inner end of plunger head 56 and the piston cork 48. Aspiration is achieved in the usual manner, i.e. by the user retracting the plunger somewhat after the initial injection, while observing the needle end of cartridge 30, to see if this retraction causes blood to be pulled into the cartridge 30. If no blood appears, the injection is continued. If blood appears, then the needle must be removed and reinserted at a different location in the tissue, in accordance with well known practice.

The opening 100 provides a way of locking the bushing 14 into position relative to the body 12 when the stop bushing is extended (FIG. 3).

The body 12 is shown to include a concave girth groove which extends entirely around body 12. This is one way of providing diametrically opposed finger receiving recess portions, each for receiving a finger. In another embodiment, it might be desirable to merely recess the outer portion of the body 12 at the finger locations.

The chamber formed between the two surfaces 80, 84 may be vented in any suitable manner. In the illustrated embodiment, this venting occurs through the opening 100.

The various parts of the syringe can be constructed from metal or plastic materials, in accordance with the state of the art at the time of construction of a particular syringe. The various parts may be secured together in any suitable manner as long as those parts which must be separated can be separated.

The invention and its attendant advantages will be understood from the foregoing description of a typical and preferred embodiment, constituting the best mode of the invention known to applicant at the time of filing of the patent application. However, it will apparent from the embodiment, and from the following claims, that various changes may be made in the form, construction, and arrangement of the parts of the syringe without departing from the spirit and scope of the invention. For example, certain features of the syringe could be incorporated in a muscle energized syringe in which thumb pressure applied to the plunger overcomes the force of a detent lock and moves the first bushing from its retracted to its extended position, attended by forward movement of the cartridge and needle, and penetration of the needle. A second detent lock may be engaged at the extended position. Accordingly, I do not wish to be restricted to the specific forms shown, or the specific use mentioned, except to the extent that the invention is defined in the accompanying claims.

I claim:

1. A self-injecting syringe, comprising:
   a finger-grip body having first and second ends and an annular sidewall defining an inner chamber, and including an outer surface grip portion adapted to be gripped by fingers of a user;
   a first bushing having a first end portion which is slidably received within said chamber, and a second end portion extendable axially from said first end portion out through the first end of said body;
   stop means for preventing movement of said bushing out from said body;
   an end wall at the second end of said body;
   a syringe barrel having a first end connected to the first end of said body, a second opposite end, and a cartridge chamber;
   a second bushing within the second end of the syringe barrel adapted for axial movement, said second bushing including a central needle receiving opening;
   an end cap at the second end of the barrel;
   a first compression spring between the end cap and the second bushing, normally biasing said second bushing rearwardly;
   a second compression spring within said inner chamber, bearing at one of its ends against said first bushing and at its opposite end against said end wall, said compression spring normally biasing said first bushing toward said stop means; and
   releasable lock means within said body, including a lock member operable to lock said first bushing into a retracted position, said second compression spring being compressed, and said first bushing being spaced axially from said stop means when said first bushing is in its retracted position, and a release trigger means positioned to be contacted by a finger positioned on the grip portion of said body, whereby finger pressure on said trigger means will unlock said lock means, releasing the second compression spring and allowing it to drive the bushing axially within said body until the bushing contacts the stop means.

2. A syringe according to claim 1, wherein said releasable lock means comprises cavity means within a side portion of the first bushing, said cavity means comprising a V-shaped floor portion having two floor parts and a radially outwardly directed apex, a V-shaped leaf spring within said cavity means having two lugs interconnected at a bight, with the angle between the lugs being smaller than the angle between the two floor parts, and with the bight of the spring being directed radially outwardly, said finger-grip body having a lock hole formed in its annular sidewall, and said leaf spring being dimensioned, and the cavity means being positioned such that when the second compression spring is compressed, and the leaf spring is at least partially relaxed, the bight of the leaf spring projects into said sidewall lock hole, and means carried by the finger-grip body for exerting an inward force on the bight of the leaf spring, for forcing it radially inwardly out from engagement with the lock hole, to in that manner free the second compression spring so that said second compression spring can drive the first bushing axially within said body until the first bushing contacts the stop means.

3. A syringe according to claim 2, wherein the trigger means comprises a trigger-plate which extends in juxtaposition with the annular sidewall of the finger-grip body, and hinge means pivotally connecting said trigger-plate to first end of the body, said trigger-plate carrying the said means for depressing the bight of the leaf spring when the trigger-plate is depressed.

4. A syringe according to claim 3, wherein the leaf spring depressing means carried by the trigger-plate comprises a radially inwardly extending lug on the inner side of the trigger-plate, radially aligned with the sidewall lock hole in the finger-grip body.

5. A syringe according to claim 4, comprising a second hole in the annular sidewall of the finger-grip body, spaced axially from the first hole and positioned such that when the first bushing is in contact with the stop means, the bight of the leaf spring is aligned with said second hole, so that the bight of the second leaf spring will project outwardly into the second hole, and lock the first bushing into position relative to the finger-grip body.

6. A syringe according to claim 5, wherein the trigger-plate comprises a second inwardly projecting lug which is aligned with the second hole in the annular sidewall of the finger-grip body.

7. A syringe according to claim 1, wherein the second bushing includes a threaded head portion at its forward end adapted to receive a threaded base portion of a hypodermic needle, wherein said threaded head portion and the central needle receiving opening in the second bushing are so positioned that when a hypodermic needle is installed, an inner fluid receiving portion of the needle projects rearwardly through the central needle receiving opening into the cartridge chamber of the syringe barrel.

8. A hypodermic syringe, comprising:
   a finger-grip member adapted to be held between two adjacent fingers of a user including sidewall means forming an axially extending inner chamber;
   an axially movable bushing within said chamber;
   first lock means for locking the bushing to the finger-grip member in a retracted position;
   second lock means for locking the bushing to the finger-grip member, in an extended position; and
   support means for a hypodermic cartridge connected to said finger-grip member; said support means including a front end member having a threaded head portion adapted for receiving a threaded base portion of a hypodermic needle and a central axial passageway for receiving an inner hollow shaft portion of the needle, and a barrel portion having an axially-extended side loading window for receiving a hypodermic cartridge into the barrel and a rear portion of the cartridge into a position to be contacted by the bushing; said support means permitting axial movement of the cartridge, the front end member, and the needle, in response to movement of the bushing from its retracted to its extended position.

* * * * *